(12) United States Patent
Boeckmann et al.

(10) Patent No.: US 11,493,522 B2
(45) Date of Patent: Nov. 8, 2022

(54) FIXED-BED REACTOR, METHOD FOR PREPARING A FIXED-BED REACTOR, AND USE OF A FIXED-BED REACTOR

(71) Applicant: Dräger Safety AG & Co. KGaA, Lübeck (DE)

(72) Inventors: Jan Boeckmann, Lübeck (DE); Stefanie Brett, Lübeck (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 194 days.

(21) Appl. No.: 15/572,950

(22) PCT Filed: May 11, 2016

(86) PCT No.: PCT/EP2016/000769
§ 371 (c)(1),
(2) Date: Nov. 9, 2017

(87) PCT Pub. No.: WO2016/180532
PCT Pub. Date: Nov. 17, 2016

(65) Prior Publication Data
US 2018/0120337 A1 May 3, 2018

(30) Foreign Application Priority Data

May 12, 2015 (DE) .................... 10 2015 005 943.2

(51) Int. Cl.
*G01N 33/98* (2006.01)
*B01J 8/02* (2006.01)
*G01N 1/22* (2006.01)

(52) U.S. Cl.
CPC ............... *G01N 33/98* (2013.01); *B01J 8/02* (2013.01); *B01J 2208/00805* (2013.01);
(Continued)

(58) Field of Classification Search
CPC .......... G01N 33/98; G01N 2001/2244; G01N 1/2214; B01J 8/02; B01J 2208/024; B01J 2208/00805
See application file for complete search history.

(56) References Cited

U.S. PATENT DOCUMENTS 3,684,456 A * 8/1972 McConnaughey .... G01N 31/22
436/132
4,791,065 A 12/1988 Rislove
(Continued)

FOREIGN PATENT DOCUMENTS

| CN | 2047375 U | 11/1989 |
| CN | 202903805 U | 4/2013 |
| EP | 2 698 201 A1 | 2/2014 |

OTHER PUBLICATIONS

IUPAC Compendium of Chemical Terminology, 2nd ed (the "Gold Book").
(Continued)

*Primary Examiner* — Lore R Jarrett
(74) *Attorney, Agent, or Firm* — McGlew and Tuttle, P.C.

(57) ABSTRACT

A fixed bed (10) is provided for a fixed-bed reactor (100). The fixed bed (10) contains a particulate carrier and at least one reactive substance. The carrier is a silicate compound and the reactive substance is an organometallic pyridine compound. A method for preparing such a fixed bed is provided. The method includes the steps of preparing the carrier, preparing an impregnation and treating the carrier with the impregnation. In addition, a gas-measuring tube is provided with a correspondingly prepared fixed bed as well. A method uses organometallic pyridinium compounds, especially pyridinium dichromate, in a fixed-bed reactor for detecting alcohol compounds and for preparing formaldehyde and/or acetaldehyde.

5 Claims, 2 Drawing Sheets

(52) U.S. Cl.
  CPC ....... *B01J 2208/024* (2013.01); *G01N 1/2214* (2013.01); *G01N 2001/2244* (2013.01)

(56) References Cited

U.S. PATENT DOCUMENTS

| | | | | |
|---|---|---|---|---|
| 5,071,769 A | * | 12/1991 | Kundu | A61B 5/083 422/413 |
| 5,747,346 A | * | 5/1998 | Pullarkat | G01N 33/66 436/127 |
| 5,834,571 A | | 11/1998 | Bernier et al. | |
| 5,958,785 A | * | 9/1999 | Pullarkat | G01N 33/98 436/127 |

OTHER PUBLICATIONS

Zhu Bing et al., Organic Synthesis, Southwest Jiaotong University Press, pp. 134-136, published Jan. 31, 2014.

* cited by examiner

FIXED-BED REACTOR, METHOD FOR PREPARING A FIXED-BED REACTOR, AND USE OF A FIXED-BED REACTOR

CROSS REFERENCE TO RELATED APPLICATIONS

This application is a United States National Phase Application of International Application PCT/EP2016/000769, filed May 11, 2016, and claims the benefit of priority under 35 U.S.C. § 119 of German Application 10 2015 005 943.2, filed May 12, 2015, the entire contents of which are incorporated herein by reference.

FIELD OF THE INVENTION

The present invention pertains to a fixed-bed reactor corresponding to FIG. 1, to a method for preparing such a fixed-bed reactor, as well as to the use of such a fixed-bed reactor, especially to the use of such a fixed-bed reactor to detect volatile organic compounds, e.g., alcohol compounds.

BACKGROUND OF THE INVENTION

Fixed-bed reactors are known, in principle. They are typically a fixed bed of particles, through which a fluid can flow (a fixed bed), which is arranged in a corresponding housing. A fixed bed is a bed in which the particles occur in an optimally dense packing corresponding to their shape and have as little freedom of movement as possible. At the same time, a gas stream can, of course, flow through the particles in this fixed bed. The particles are usually used as carriers for at least one reactive substance. The reactive substance is typically such that it can react with a defined substance, which is present in the fluid, when the fluid is flowing by the particle in question. Such fixed-bed reactors are used, for example, in gas-measuring tubes (tubes), for example, in the form of the applicant's products commercially available under the trademark "Dräger Röhrchen"®. Such a gas-measuring tube comprises, for example, a transparent housing with a first end and with a second end, so that a fluid can flow through the housing. A corresponding fixed bed, which can be fixed in the housing, for example, by means of a wire mesh, is located in the housing.

In addition to a wide variety of applications in industry—for example, to detect various short-chain alcohol compounds, e.g., methyl alcohol, ethyl alcohol, propyl alcohol or butyl alcohol—a prior-art example of application of such gas-measuring tubes is the detection of breath alcohol. The gas-measuring tube is now inserted into a device, into which a test subject can blow. The breath of the test subject then flows through the tube. The fixed bed is configured in this case such that a reaction can take place with alcohol. If a corresponding quantity of alcohol is present in the breath of the test subject, a color change reaction takes place in the area of the fixed-bed reactor, and this reaction is correspondingly optically detectable.

The color change reaction is typically based on a redox reaction with the involvement of chromium salts, for example, a redox reaction while chromium(VI) is reduced to chromium(III).

One drawback of such reactions is, however, the relatively high hazard potential for humans and the environment due to many of the chromium compounds suitable, in principle, for such a detection, especially inorganic chromium compounds. The industrial processing of inorganic chromium compounds is therefore often only possible if very strict safety standards are complied with and if increased safety measures are taken. The preparation of fixed-bed reactors that contain such compounds may therefore be very complicated and costly.

SUMMARY OF THE INVENTION

Based on this, an object of the present invention is to overcome these and other drawbacks of the state of the art and to create an improved fixed-bed reactor. This shall be able to be prepared in a cost-effective and simple manner.

To accomplish this object, the present invention provides a fixed-bed reactor, as well as a method for preparing a fixed bed for such a fixed-bed reactor. A gas-measuring tube is also provided with such a fixed-bed reactor. A method uses of organometallic pyridinium compounds in a fixed-bed reactor.

In case of a fixed bed for a fixed-bed reactor, wherein the fixed bed has a particulate carrier and at least one reactive substance and wherein the carrier is silica compound, the present invention makes provisions for the reactive substance to be an organometallic pyridine compound.

A fixed-bed reactor with such a fixed bed can be used with great advantage for various purposes. It is thus conceivable that the fixed bed is present as a detection reagent for a substance that is present in a gas stream that is passed through the fixed-bed reactor. In other words, the fixed bed may be used as an indicator layer. If the substance in question is present in the gas stream, an optically detectable reaction can take place due to the reaction of this substance with the reactive substance bound to the fixed bed. The detection of alcohol substances is especially easily possible above all in his connection by means of the reactive substance according to the present invention.

It is also conceivable that the fixed-bed reactor is used to synthesize substances, in which case the fixed bed provides the reactive substance and the educts to be reacted are sent to the reactive substance by means of a gas stream. The reactive substance is bound according to the present invention to the carrier, so that the reaction of the educts takes place on the surface of the particulate carrier. The products formed in the process are again released from the fixed-bed reactor with the gas stream flowing off. This offers the special advantage that the reactive substance does not subsequently have to be separated from the product any longer. Especially the synthesis of formaldehyde or acetaldehyde is especially easily possible in this connection by means of the reactive substance according to the present invention. A substance thus produced may be used, for example, as a reagent in another indicator layer arranged downstream. It is thus conceivable, for example, that a first layer, in which formaldehyde is produced, and a second layer, in which the formaldehyde is used as a reagent for detection, are arranged in a housing of a fixed-bed reactor.

It is thus seen that it is especially advantageous in the sense of the present invention if the reactive substance is an organometallic pyridine compound.

Such compounds may show a marked color change especially in a reaction with alcohols. At the same time, formaldehyde and/or acetaldehyde may be released during this reaction. Thus, both the detection of alcohols in a gas mixture, e.g., in a breathing gas stream, and the synthesis of formaldehyde and/or acetaldehyde are possible by means of a fixed-bed reactor according to the present invention. At the same time, organometallic pyridine compounds offer the advantage that they are substantially less hazardous for the environment or even toxic than, for example, inorganic chromium compounds. In addition, it could be surprisingly observed that they may also be markedly more effective in terms of their redox activity than inorganic chromium compounds.

In a preferred embodiment, a fixed-bed reactor according to the present invention may thus be a tube for determining breath alcohol. It is also conceivable that a fixed-bed reactor according to the present invention is a tube for determining short-chain alcohols in a gas mixture. For example, the fixed-bed reactor according to the present invention may be a tube for determining methyl alcohol, ethyl alcohol, propyl alcohol or butyl alcohol. In any case, the housing of such a tube may be formed by a glass tube, in which the fixed bed is correspondingly arranged. The fixed bed may be arranged here, for example, between a first holding device and a second holding device in the tube, i.e., in the housing. The holding devices may be, for example, wire mesh or the like. A glass tube has the advantage in this connection that it is transparent. A color change reaction, which takes place in the fixed bed, can therefore be observed from the outside. It is, of course, also conceivable that the housing consists of a transparent plastic, for example, a plastic tube.

In another preferred embodiment, a fixed-bed reactor according to the present invention may be a device for producing formaldehyde and/or acetaldehyde.

The particulate carrier of the fixed bed may be formed in any case by silica particles (silica gel). These silica particles, i.e., the particulate carrier, can then be impregnated with the reactive substance. It is, of course, also conceivable that the silica particles are additionally impregnated with additional substances. However, this is not absolutely necessary. Silica particles are defined in this connection as granular particles, which consist of a silica compound. The particulate carrier of the fixed bed thus consists of a silica compound. Silica particles have a certain transparency, so that a color change can readily be observed. A great advantage of silica particles is, in addition, that they are chemically inert. Both amorphous, nanoporous and nonporous silica are suitable. Amorphous, nanoporous silica is preferred.

It proved to be especially advantageous if the pyridine compound is selected from among pyridinium chlorochromate, pyridinium dichromate and bispyridine chromium trioxide, preferably pyridinium dichromate. On contact with breath alcohol, a marked color change from yellow to green is displayed especially by pyridinium dichromate. Other detectable gaseous compounds are, for example, 2-propyl alcohol, ethylene oxide, dichloromethane, vinyl chloride and/or chloroform. The use of pyridine compounds offers many advantages in this connection. Thus, the fixed-bed reactors according to the present invention surprisingly have a markedly increased long-term stability. Furthermore, the detection can be carried out unambiguously even with a relatively small quantity of reactive substance. The fixed-bed reactors according to the present invention can, in addition, surprisingly be used reliably in very broad temperature and humidity ranges. In particular, they are relatively insensitive to the introduction of water or moisture.

It also proved to be advantageous in this connection if the carrier is impregnated with the reactive substance. The reactive substance is therefore arranged on the surface of the carrier. A gas stream, which flows through between the carrier particles, can thus flow past the reactive substance. For example, alcohol contained in the gas stream can then react correspondingly with the pyridine compound. It is especially favorable in this connection if the carrier is a carrier that is produced by mixing silica particles with an impregnating solution and mixing them with one another during mechanical agitation. The impregnating solution is a solution of the organometallic pyridine compound according to the present invention in a solvent. The solvent contains, for example, an inorganic phosphorus compound. Such a phosphorus compound may be selected, for example, from among phosphinic acid, phosphonic acid and/or phosphoric acid. It is also conceivable in this connection that the solvent additionally contains another acid and/or an acid anhydride. This additional acid may be, for example, sulfuric acid, the additional acid anhydride may be, for example, acetic anhydride. The color reaction may be markedly increased further and the sensitivity of the detection can be increased by the additional addition of acid anhydride. The acid anhydride is preferably added in a catalytic quantity. It is conceivable, for example, that a quantity not exceeding 500 µL, preferably not exceeding 300 µL, is added to a batch of 100 g. It also proved to be favorable, especially for the detection of alcohol compounds in a gas mixture, if the carrier is a carrier that is produced by mixing silica particles with an impregnating solution, mixing them during mechanical agitation and subsequently heating them. The impregnating solution is a mixture of a solvent in this case, which contains an inorganic phosphorus compound and optionally an additional acid and/or acid anhydride, with a reactive substance, namely, an organometallic pyridine compound. The inorganic phosphorus compound is preferably phosphoric acid, the additional acid is sulfuric acid, the acetic anhydride is acetic anhydride, and the organometallic pyridine compound is pyridinium dichromate.

It was surprisingly found that it is favorable if the carrier contains a charge of the organometallic pyridine compound in a quantity of at most 10 wt. %, preferably at most 5 wt. %, especially preferably at most 2 wt. % or less. It is seen that a special advantage of the solution according to the present invention is that only a very small quantity of the organometallic pyridine compound is needed for an effective and reliable detection. This is especially advantageous when the pyridine compound is a chromate compound. The chromate content may be, on the whole, markedly lower than <0.1%.

It is, furthermore, favorable if the silica compound is a silica gel with a particle size distribution of at least 0.1 mm to at most 1.5 mm. The particle size distribution is defined here as the range of the sizes of the individual particles occurring in the carrier. In case of a particle size distribution of 0.1 mm to 1.5 mm, the carrier therefore contains particles with a size of 0.1 mm as the smallest particles and particles with a size of 1.5 mm as the largest particles. In addition, the carrier may contain particles of all conceivable sizes in between. It is obvious that different variants of the particle size distribution are conceivable within the framework of the present invention. It is not necessary for the entire range from at least 0.1 mm to at most 1.5 mm to be always covered. It is rather definitely conceivable that only a range within this specified range is achieved for different exemplary embodiments. It is thus also conceivable that the carrier is a silica gel with a relatively narrow and homogeneous particle size distribution, for example, between 0.1 mm and 0.4 mm, and preferably between 0.2 mm and 0.3 mm. A silica gel with a relatively broad particle size distribution, for example, between 0.6 mm and 1.4 mm and preferably 0.8 mm to 1.2 mm is also conceivable. For example, the flow resistance offered by the fixed-bed reactor to a gas stream can be influenced by selecting the particle size distribution.

In another aspect, the present invention pertains to a method for preparing a fixed bed for a fixed-bed reactor, comprising the steps of
a. preparing a carrier,
b. preparing an impregnation,
c. treating the carrier with the impregnation,
wherein the impregnating solution, which is provided in step b, is a solution of an organometallic pyridine compound in a solvent that contains an inorganic phosphorus compound.

The treatment of the carrier with an impregnating solution, which contains a solvent with an inorganic phosphorus compound in addition to the organometallic pyridine compound according to the present invention, has, in particular, surprisingly the effect that the carrier particles treated with this solution are suitable for a highly effective reaction of alcohol compounds. It is possible in this manner, for example, to react relatively small quantities of alcohol in a gas sample. The alcohol contained is surprisingly reacted now nearly completely, so that a fixed bed prepared by means of this method can be used for both the quantitative detection of alcohol and for the synthesis of products formed during the reaction, e.g., formaldehyde or acetaldehyde.

Provisions are made in a preferred embodiment for the inorganic phosphorus compound to be a phosphate compound, which is selected from among phosphinic acid, phosphonic acid and/or phosphoric acid, and preferably phosphoric acid. The use of phosphoric acid, in particular, offers the great advantage that it is not released in a gaseous form later during the flow through the fixed bed.

Provisions are made in yet another embodiment for the solvent of the impregnating solution to contain at least one additional acid, preferably sulfuric acid. It is, of course, also conceivable that the solvent of the impregnating solution contains both sulfuric acid and a phosphate compound, preferably a mixture of sulfuric acid and phosphoric acid. It is conceivable in this connection in any case that the solvent of the impregnating solution is a mixture of phosphoric acid and sulfuric acid at a ratio of at least 3:1 and at most 1:3. It is, of course, also conceivable that the mixture of phosphoric acid and sulfuric acid is present at a ratio of at least 2:1 and at most 1:2 or at a ratio of 1:1.

It is also conceivable that the solvent of the impregnating solution contains at least one additive in the form of an acid anhydride. The acid anhydride is acetic anhydride in a preferred example, and other acid anhydrides are, of course, also conceivable. It is favorable if the percentage of phosphoric acid is higher than the percentage of the acid anhydride. It is therefore favorable if the solvent of the impregnating solution is a mixture of phosphoric acid and acetic anhydride at a ratio of at least 50:1 and at most 5:1. It is especially favorable if the solvent of the impregnating solution is a mixture of phosphoric acid and acetic anhydride at a ratio of at least 25:1 and at most 15:1.

It was always found to be especially favorable if the preparation of the impregnation includes the dissolution of the organometallic pyridinium compound in an aqueous solution, which contains at least 50% of phosphoric acid. An impregnating solution according to the present invention may thus be an impregnating solution that contains an aqueous solvent containing at least 50% of phosphoric acid, an organometallic pyridinium compound and additionally another acid. For example, the impregnating solution may be a mixture of an aqueous solvent containing at least 50% of phosphoric acid as well as sulfuric acid as an additional acid and pyridinium chlorochromate, pyridinium dichromate or bispyridine chromium trioxide as an organometallic pyridinium compound. It is conceivable in this connection, in particular, that the impregnating solution is a mixture of an aqueous solvent with at least 50% of phosphoric acid, additionally sulfuric acid and pyridinium dichromate, which is dissolved in the solution of phosphoric acid and sulfuric acid. It is, of course, also conceivable, however, that the impregnating solution contains a higher percentage of phosphoric acid or even consists entirely of phosphoric acid. In other words, it is also conceivable that the preparation of the impregnation includes the dissolution of the organometallic pyridinium compound in an aqueous solvent that contains at least 50% and at most 100% of phosphoric acid.

It is preferred in this connection if the concentration of the pyridinium compound in the solvent is at least 0.001 mol/L, preferably at least 0.05 mol/L and especially preferably at least 0.50 mol/L. It is further preferred for the concentration of the pyridinium compound in the solvent to be at most 0.50 mol/L, preferably at most 0.05 mol/L and especially preferably at most 0.02 mol/L.

It is thus seen that the concentration of the pyridinium compound in the solvent is at least 0.001 mol/L and at most 0.50 mol/L, preferably at least 0.005 mol/L and at most 0.05 mol/L, especially preferably at least 0.01 mol/L and at most 0.02 mol/L. It is, of course also conceivable that the concentration of the pyridinium compound in the solvent is at least 0.001 mol/L and at most 0.05 mol/L, at least 0.001 mol/L and at most 0.1 mol/L, at least 0.005 mol/L and at most 0.1 mol/L, at least 0.005 mol/L and at most 0.02 mol/L, at least 0.01 mol/L and at most 0.1 mol/L, or at least 0.01 mol/L and at most 0.05 mol/L.

It was furthermore found to be advantageous when preparing the fixed bed according to the present invention for the treatment of the carrier with the impregnation to comprise the following steps:
c.1 mixing of the carrier with the impregnation;
c.2 mixing of the carrier with the impregnation with mechanical agitation;
c.3 optionally: heating of the mixture; and
c.4 optionally: repeated mixing of the mixture.

It is conceivable in this connection both that the treatment of the carrier has only the steps c.1 and c.2 and that the treatment of the carrier has the steps c.1, c.2 and c.3 or the steps c.1, c.2 and c.4 or the steps c.1, c.2, c.3 and c.4.

The mixing of the carrier with the impregnating solution according to step c.1 may, however, be carried out in the simplest case by the impregnating solution being simply added as a liquid to the solid carrier prepared. For example, the impregnating solution may be charged into a closable vessel by charging in the particulate solid carrier in advance. This vessel may subsequently be closed. The mixing of the carrier and of the impregnation may then be carried out, for example, on a shaker (shaking mixer).

The heating of the mixture according to step c.3 may be carried out, for example, at a temperature of at least 50° C. to at most 120° C. The heating is preferably carried out at a temperature between about 60° C. and about 90° C., for example, at 80° C. It is favorable in this connection if the heating is carried out, for example, in a rolling drying oven, i.e., with agitation. The duration of step c.3 may range from a few hours to several days.

The mixing of the mixture according to c.4 may, in turn, be carried out by means of the above-mentioned shaker (shaking mixer).

Provisions are, however, made in any case for the impregnating solution and the carrier to be mixed with one another in step c.1 at a ratio of at least 0.2 mL of impregnating solution per g of carrier, preferably at least 0.4 mL of impregnating solution per g of carrier, and especially preferably at least 0.7 mL per g of carrier. In addition, provisions are made for the impregnating solution and the carrier to be mixed with one another in step c.1 at a ratio of at most 1.0 mL of impregnating solution per g of carrier, preferably at most 0.7 mL of impregnating solution per g of carrier, and especially preferably at most 0.05 mL of impregnating solution per g of carrier. It is thus seen that it is favorable if the impregnating solution and the carrier are mixed with one another in step c.1 at a ratio of at least 0.05 mL of impregnating solution per g of carrier and at most 1.0 mL of impregnating solution per g of carrier. It is also conceivable that the impregnating solution and the carrier are mixed with one another in step c.1 at a ratio of at least 0.05 mL and at most 0.7 mL or at a ratio of at least 0.05 mL and at most 1 mL or at a ratio of at least 0.4 mL and at most 1 mL or at a ratio of at least 0.7 mL and at most 1 mL or at a ratio of at least 0.4 mL and at most 0.7 mL or at a ratio of at least 0.7 mL and at most 1.0 mL or at a ratio of 0.4 mL and at most 1.0 mL or at a ratio of at least 0.7 mL and at most 1.0 mL of impregnating solution per g of carrier.

In any case, the charging with the organometallic pyridine compound that can be reached in this manner is at most 10 wt. %, preferably at most 5 wt. %, especially preferably at most 2 wt. % or less. If the impregnating solution is an impregnating solution as was described above, i.e., it has a pyridinium compound concentration of at least 0.001 mol/L and at most 0.50 mol/L, it was found that 1 mmole of analyte, for example, 1 mmole of ethyl alcohol, can be reached with a charge of less than 1 mmole of the pyridine compound. In particular, the pyridinium compound may be charged at a molar ratio between 0.25 mmole and 0.60 mmole per mmole of analyte. This applies especially if the pyridinium compound is pyridinium dichromate.

In another aspect, the present invention pertains to a gas-measuring tube with a fixed bed according to the present invention. Such a gas-measuring tube is used as a fixed-bed reactor. It typically comprises a housing, in which the fixed bed is filled. The housing is, for example, a glass tube with a first end and with a second end. A special advantage of glass tubes is the transparency of the material of the housing. It is, of course, also conceivable that the housing consists of a material other than glass, as long as the color change taking place in the fixed bed can be observed through the wall of the housing, i.e., it is advantageous if the housing has a transparent wall. A gas sample to be tested can flow through the first end into the glass tube and it can again flow out through the second end. The gas sample to be tested may be, for example, a breathing gas sample. It is thus conceivable that a test subject, whose breath shall be tested for the possible presence of alcohol, shall blow into such a gas-measuring tube. However, other applications are, of course, conceivable as well.

The fixed bed is preferably arranged between two holding elements in the housing. It is also conceivable that additional fixed bed layers are also arranged in the housing in addition to the fixed bed according to the present invention and the holding elements. For example, an additional fixed bed layer may be used to remove water from the gas mixture to be tested before the gas mixture flows through the fixed bed according to the present invention, which is impregnated with the organometallic pyridinium compound.

It is consequently seen that it is advantageous in the sense of the present invention if a gas-measuring tube has a fixed bed, wherein the fixed bed has a particulate carrier and at least one reactive substance, the carrier being a silicate compound and the reactive substance being an organometallic pyridine compound. It is, furthermore, advantageous if the pyridine compound is selected from among pyridinium chlorochromate, pyridinium dichromate and bispyridine chromium trioxide, preferably pyridinium dichromate. It is especially favorable if the carrier is impregnated with the reactive substance such that the carrier has a charge of an organometallic pyridine compound of at most 10 wt. %, preferably at most 5 wt. %, especially preferably at most 2 wt. % or less. For example, a reaction of alcohol can take place in this manner with a charge of about 0.25 mmol to 0.6 mmol of pyridinium dichromate per mmole of alcohol to be detected. It is also advantageous in another aspect if the silica compound is a silica gel with a particle size distribution of less than 0.1 mm to at most 1.5 mm.

The present invention pertains, in addition, to the use of organometallic pyridinium compounds, especially pyridinium dichromate, in a fixed-bed reactor for detecting alcohol compounds. The present invention pertains, furthermore, to the use of organometallic pyridinium compounds, especially pyridinium dichromate, in fixed-bed reactors for preparing formaldehyde and/or acetaldehyde. The use of the organometallic pyridinium compounds takes place in both cases corresponding to what was already described above, i.e., the organometallic pyridinium compound is preferably applied (impregnated) to a carrier consisting of a silica compound, so that the carrier has, for example, a charge of pyridinium dichromate in a quantity of at most 10 wt. %, preferably at most 5 wt. %, preferably at most 2 wt. % or less. The carrier thus coated may then be introduced into a housing of a fixed-bed reactor, for example, by pouring. If a gas stream is then passed through the housing, it can flow through the fixed bed. Analytes contained in the gas stream, for example, alcohol, but also 2-propyl alcohol, ethylene oxide, dichloromethane, vinyl chloride or chloroform, can then react with the organometallic pyridine compound contained in the fixed bed. On the one hand, alcohol will now react to form formaldehyde. On the other hand, an optically detectable color change takes place, which indicates the presence of the analyte in question.

Further features, details and advantages of the present invention appear from the text of the claims as well as from the following description of exemplary embodiments on the basis of the drawings. The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
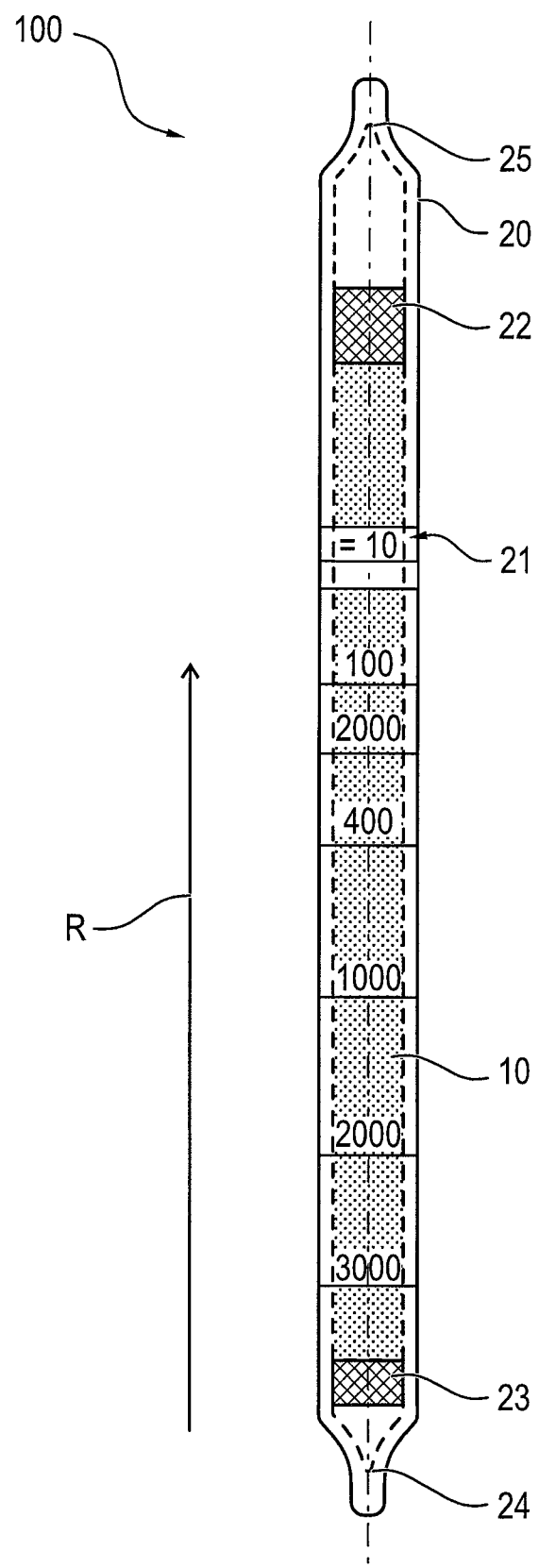
FIG. 1 is a schematic view of a fixed-bed reactor according to the present invention, namely, of a gas-measuring tube with a fixed bed according to the present invention.

Referring to the drawings, it is seen in FIG. 1 that a fixed-bed reactor 100 according to the present invention has a housing 20, in which a fixed bed 10 according to the present invention is arranged. The housing 20 is tubular with a first end and with a second end. The first end is used as a gas inlet 25. The second end is used as a gas outlet 24. The gas inlet 25 and the gas outlet 24 are closed at first by small glass caps in the exemplary embodiment shown in FIG. 1. These can be broken up when the fixed-bed reactor 100 is to be used. If the gas inlet 25 and the gas outlet 24 are opened, a gas sample can flow through the gas inlet 25 into the fixed-bed reactor 100 and through the fixed bed 10 and flow out again of the fixed-bed reactor 100 through the gas outlet 24. A graduation 21 is applied to the housing. A color change takes place in case of a reaction of analytes contained in the gas sample with the reactive substance of the fixed bed 10. The color change takes place first in the vicinity of the gas inlet 25 and then continues in the direction of the gas outlet 24. Depending on the concentration at which the analyte is contained in the gas sample, the length of the section is shorter or longer in the direction R (it must be rotated by 180° in the figure because the direction of flow is from top to bottom) in which the color change spreads. The length of this section can then be determined by means of the graduation 21 and the concentration at which the analyte is present can be inferred.

The fixed bed 10 is present as a bed in the housing 20. It is fixed in the housing 20 by means of a first holding element 23 and a second holding element 22. The fixed bed 10 consists of a particulate carrier, which contains a reactive substance. The carrier consists of silica particles, which have a size between at least 0.1 mm and at most 1.5 mm. The silica particles are impregnated with the reactive substance. The reactive substance is an organometallic pyridine compound. In a first exemplary embodiment, the reactive substance is pyridinium dichromate. The carrier has a charge of at most 2 wt. % of pyridinium dichromate. In any case, the fixed bed 10 is prepared by the carrier having been treated with an impregnating solution, which contains a solution of an organometallic pyridine compound, namely, pyridinium dichromate, in a solvent, the solvent being an inorganic phosphorus compound, namely, phosphoric acid.

Figure 2:
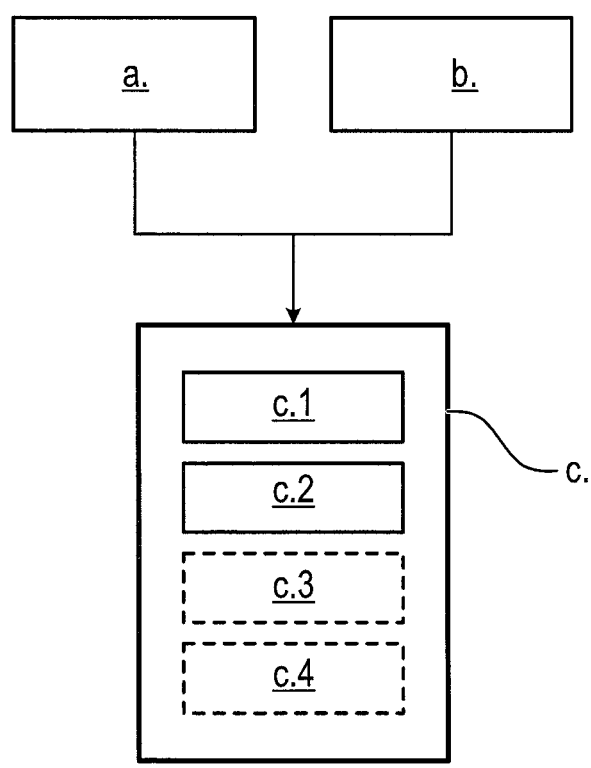
FIG. 2 is a schematic view of the course of a method according to the present invention for preparing a fixed bed according to the present invention.

FIG. 2 shows a schematic view of such a method for preparing a corresponding fixed bed 10. The method has the steps of
a. preparing a carrier,
b. preparing an impregnation, and
c. treating the carrier with the impregnation.

The impregnation, which is provided in step b., is a solution of an organometallic pyridine compound in a solvent that contains an inorganic phosphorus compound. In one exemplary embodiment, the organometallic pyridine compound is pyridinium dichromate, and the inorganic phosphorus compound is phosphoric acid. The impregnating solution (the impregnation) further contains in one exemplary embodiment an additional acid, namely, sulfuric acid. The sulfuric acid and the phosphoric acid are present at a ratio of 1:1. In addition to the sulfuric acid and the phosphoric acid, which are present as aqueous acids each, no additional components are present in the solvent of the impregnating solution in this exemplary embodiment, i.e., the impregnating solution has an aqueous solvent, which contains at least 50% of phosphoric acid.

In another variant, the organometallic pyridine compound is likewise pyridinium dichromate, and the inorganic phosphorus compound is phosphoric acid. Further, the impregnating solution (the impregnation) contains in one exemplary embodiment an acid anhydride, namely, acetic anhydride. The acetic anhydride and the phosphoric acid are present at a ratio of 1:20. The impregnating solution has an aqueous solvent here as well, which contains at least 50% of phosphoric acid.

The treatment of the carrier with the impregnation corresponding to step c. has the steps c.1 and c.2. The carrier is mixed with the impregnation in step c.1. According to step c.2, the carrier is mixed with the impregnation under mechanical agitation. Step c. optionally has, in addition, the optional features described in steps c.3 and c.4. The mixture of carrier and impregnation is heated in step c.3, i.e., it is exposed to a temperature of at least 50° C. to at most 120° C. for a certain time, while both may continue to the agitated at the same time. For example, the heating may be carried out in a rolling drying oven. The mixed and heated mixture is mixed once again in step C4. The mixture cools in the process.

EXAMPLE 1

Corresponding to step a. of the method according to the present invention, a carrier is prepared by weighing 100 g of an amorphous, nanoporous silica with a particle size distribution of 0.8-1.2 mm into an appropriate vessel.

An impregnation is prepared according to step b. by dissolving 0.37 g of pyridinium dichromate in a solvent consisting of 44.0 mL of $H_2SO_4$ and 44.0 mL of $H_3PO_4$.

The carrier is then mixed corresponding to step c. of the method according to the present invention with the impregnation by charging the impregnation with the carrier into the vessel. The mixture thus prepared is mixed on a shaking mixer for 20 minutes.

The fixed bed 10 thus prepared is then filled into a glass tube, so that a fixed-bed reactor 100 with a fixed bed 10, namely, a gas-measuring tube, is obtained.

EXAMPLE 2

Corresponding to step a. of the method according to the present invention, a carrier is prepared by weighing 100 g of an amorphous, nanoporous silica with a particle size distribution of 0.2-0.3 mm into an appropriate vessel.

An impregnation is prepared according to step b. by dissolving 0.25 g of pyridinium dichromate in a solvent consisting of 6.0 mL of $H_3PO_4$.

The carrier is then mixed corresponding to step c. of the method according to the present invention with the impregnation by adding the impregnation to the carrier in the vessel. The mixture thus prepared is mixed on a shaking mixer for 20 minutes. The mixture is then heated for several days at a temperature of 80° C. in a rolling drying oven. The mixture is then mixed again on the shaking mixer at room temperature until it is rather cold.

The fixed bed 10 thus prepared is then filled into a glass tube, so that a fixed-bed reactor 100 with a fixed bed 10, namely, a gas-measuring tube, is obtained.

EXAMPLE 3

Corresponding to step a. of the method according to the present invention, a carrier is prepared by weighing 100 g of an amorphous, nanoporous silica with a particle size distribution of 0.2-0.3 mm into an appropriate vessel.

According to step b., an impregnation is prepared by dissolving 0.25 g of pyridinium dichromate in a solvent consisting of 6.0 mL of $H_3PO_4$ and 284 µL of acetic anhydride.

The carrier is then mixed with the impregnation corresponding to step c. of the method according to the present invention by adding the impregnation to the carrier in the vessel. The mixture thus prepared is mixed on a shaking mixer for 20 minutes. The mixture is then heated for several days at a temperature of 80° C. in a rolling drying oven. The mixture is then mixed again on the shaking mixer at room temperature until it is rather cold.

The fixed bed 10 thus prepared is then filled into a glass tube, so that a fixed-bed reactor 100 with a fixed bed 10, namely, a gas-measuring tube, is obtained.

The present invention is not limited to one of the above-described embodiments but can be modified in many different ways.

All the features and advantages appearing from the claims, the description and the drawings, including design details, arrangements in space and method steps, may be essential for the present invention both in themselves and in the many different combinations.

While specific embodiments of the invention have been shown and described in detail to illustrate the application of the principles of the invention, it will be understood that the invention may be embodied otherwise without departing from such principles.

The invention claimed is:

1. A gas-measuring tube comprising:
a housing;
a particulate carrier in the housing; and
at least one reactive substance, wherein the carrier is a silica compound and the at least one reactive substance is an organometallic pyridine compound, the organometallic pyridine compound being one of pyridinium chlorochromate, pyridinium dichromate and bispyridine chromium trioxide, wherein the carrier is impregnated with an impregnation, the impregnation comprising a solvent, the organometallic pyridinium compound being dissolved in the solvent and the solvent comprising phosphoric acid or an aqueous solvent that contains at least 50% phosphoric acid, the carrier having a concentration of the organometallic pyridine compound of at most 10 weight percent, wherein the solvent comprises at least one additive, the at least one additive comprising an acid anhydride, the acid anhydride being acetic anhydride, wherein a percentage of phosphoric acid in the solvent is greater than a percentage of the acetic anhydride in the solvent.

2. The gas measuring tube in accordance with claim 1, wherein the silica compound is a silica gel with a particle size distribution of at least 0.1 mm to at most 1.5 mm.

3. A method comprising the steps of:
providing a fixed bed having a particulate carrier and at least one reactive substance and the carrier is a silica compound, wherein the reactive substance is an organometallic pyridine compound, the organometallic pyridine compound is selected from pyridinium chlorochromate, pyridinium dichromate and bispyridine chromium trioxide; and
impregnating the carrier by treating the carrier with a solvent comprising the organometallic pyridinium compound dissolved in the solvent, wherein the solvent comprises phosphoric acid or an aqueous solvent that contains at least 50% phosphoric acid and the carrier has a concentration of the organometallic pyridine compound of at most 10 weight percent, wherein the solvent comprises at least one additive, the at least one additive comprising an acid anhydride, the acid anhydride being acetic anhydride, wherein a percentage of phosphoric acid in the solvent is greater than a percentage of the acetic anhydride in the solvent.

4. The method according to claim 3, further comprising preparing formaldehyde and/or acetaldehyde via the fixed bed reactor.

5. The method according to claim 3, further comprising detecting alcohol compounds with the fixed-bed reactor.

* * * * *